US012667681B2

(12) United States Patent
Bartels et al.

(10) Patent No.: US 12,667,681 B2
(45) Date of Patent: Jun. 30, 2026

(54) INVERTED NOZZLE FIXTURE AND METHOD

(71) Applicant: INVOX BELGIUM NV, Diepenbeek (BE)

(72) Inventors: Frank Bartels, Hattingen (DE); Juergen Rawert, Cologne (DE)

( * ) Notice: Subject to any disclaimer, the term of this patent is extended or adjusted under 35 U.S.C. 154(b) by 669 days.

(21) Appl. No.: 18/000,397

(22) PCT Filed: Jun. 25, 2021

(86) PCT No.: PCT/EP2021/067493
§ 371 (c)(1),
(2) Date: Dec. 1, 2022

(87) PCT Pub. No.: WO2021/260179
PCT Pub. Date: Dec. 30, 2021

(65) Prior Publication Data
US 2023/0248924 A1 Aug. 10, 2023

Related U.S. Application Data

(60) Provisional application No. 63/044,368, filed on Jun. 26, 2020.

(30) Foreign Application Priority Data

Jun. 26, 2020 (EP) ..................................... 20182556

(51) Int. Cl.
*A61M 15/08* (2006.01)
*A61M 11/00* (2006.01)
(Continued)

(52) U.S. Cl.
CPC .......... *A61M 15/08* (2013.01); *A61M 11/007* (2014.02); *A61M 16/208* (2013.01);
(Continued)

(58) Field of Classification Search
CPC ............ A61M 15/00; A61M 15/06–08; A61M 11/00–003; A61M 11/006–008; A61M 11/06; B05B 15/65
See application file for complete search history.

(56) References Cited

U.S. PATENT DOCUMENTS 9,027,967 B2 * 5/2015 Geser ...................... B05B 15/18
285/334.3
9,757,750 B2 * 9/2017 Holakovsky .......... B05B 11/026
(Continued)

FOREIGN PATENT DOCUMENTS

CA      1204129 A     5/1986
CN   101426586 A     5/2009
(Continued)

OTHER PUBLICATIONS

International search report and written opinion of International patent application No. PCTEP2021067493, 11 pages.
(Continued)

*Primary Examiner* — Rachel T Sippel
(74) *Attorney, Agent, or Firm* — Synergy IP Group AG

(57) ABSTRACT

The invention provides for device for clamping a fluidic component which is subjected to a fluctuating fluid pressure, said fluidic component having a downstream end, an opposite upstream end and an outer contour, said device comprising a holder, an elastomeric shaped part and a mating part, wherein the elastomeric shaped part comprises at least one compensating surface, and wherein the at least one compensating surface in the assembled state does not contact the mating part or the at least one projection of the mating part.

25 Claims, 5 Drawing Sheets

(51) Int. Cl.
  *A61M 16/20* (2006.01)
  *B05B 15/65* (2018.01)

(52) U.S. Cl.
  CPC ..... *B05B 15/65* (2018.02); *A61M 2205/8281* (2013.01); *A61M 2207/00* (2013.01)

(56) References Cited

U.S. PATENT DOCUMENTS

| | | | |
|---|---|---|---|
| 2004/0164186 A1 | 8/2004 | Kladders | |
| 2005/0077392 A1 | 4/2005 | Geser et al. | |
| 2005/0194472 A1 | 9/2005 | Geser et al. | |
| 2007/0246573 A1 | 10/2007 | Jaunay | |
| 2010/0154972 A1 | 6/2010 | Herko et al. | |
| 2012/0260913 A1 | 10/2012 | Bach et al. | |
| 2014/0053835 A1* | 2/2014 | Gilbert | A61M 15/009 |
| | | | 128/203.14 |
| 2016/0144138 A1 | 5/2016 | Hausmann et al. | |
| 2020/0197638 A1 | 6/2020 | Bartels et al. | |
| 2021/0220575 A1* | 7/2021 | Bartels | A61M 11/007 |

FOREIGN PATENT DOCUMENTS

| | | | |
|---|---|---|---|
| DE | 102004001451 A1 | 8/2005 | |
| EP | 0627230 B1 | 2/2000 | |
| EP | 0853498 B1 | 3/2002 | |
| EP | 3615111 A1 | 11/2018 | |
| JP | S59026166 A | 2/1984 | |
| JP | 2003513817 A | 4/2003 | |
| JP | 2007517646 A | 7/2007 | |
| JP | 2020517385 A | 6/2020 | |
| RU | 2195965 C2 | 8/1997 | |
| WO | 9730743 A2 | 8/1997 | |
| WO | 0134305 A1 | 5/2001 | |
| WO | 2003097139 A1 | 11/2003 | |
| WO | 2005065836 A1 | 7/2005 | |
| WO | 2007126382 A1 | 11/2007 | |
| WO | 2012007315 A1 | 1/2012 | |
| WO | 2018197730 A1 | 11/2018 | |
| WO | 2019102002 A1 | 5/2019 | |
| WO | 2020094761 A1 | 5/2020 | |

OTHER PUBLICATIONS

Office Action issued in Russia application No. 2022130788, Jan. 24, 2025, 39 pages.

Office Action issued in Japan application No. 2022-577441, Jul. 23, 2025, 17 pages.

Search Report issued in Japan application No. 2022-57441, Jun. 13, 2025, 35 pages.

Search Report issued in China application No. 202180043914.4 , Nov. 13, 2025, 2 pages.

Office Action issued in Taiwan application No. 110123467, Nov. 14, 2025, 23 pages.

* cited by examiner

INVERTED NOZZLE FIXTURE AND METHOD

CROSS REFERENCE TO RELATED APPLICATIONS

This application is a United States National Stage Application filed under 35 U.S.C. § 371 claiming the benefit of PCT Application No. PCT/EP2021/067493, filed on Jun. 25, 2021, which claims priority to and the benefit of U.S. Provisional Application Ser. No. 63/044,368, filed on Jun. 26, 2020, and EP Application Serial No. 20182556.9, filed on Jun. 26, 2020, all of which are hereby incorporated by reference herein in their entireties.

FIELD OF THE INVENTION

The present invention is in the field of fluidic components for inhalation devices. More particularly, the invention relates to a device for clamping a miniaturized fluidic component such as a nozzle which is subjected to a fluctuating fluid pressure under standard operation. The invention further relates to inhalation devices for the inhalative administration of medically active liquids, wherein the inhalation device comprises such a clamping device.

BACKGROUND OF THE INVENTION

Nebulizers or other aerosol generators for liquids are known from the art since a long time ago. Amongst others, such devices are used in medical science and therapy. There, they serve as inhalation devices for the application of active ingredients in the form of aerosols, i.e. small liquid droplets embedded in a gas. Such an inhalation device is known e.g. from document EP 0 627 230 B1. Essential components of this inhalation device are a reservoir in which the liquid that is to be aerosolized is contained; a pumping unit for generation of a pressure being sufficiently high for nebulizing; as well as an atomizing device in the form of a nozzle.

An improvement of such an inhalation device is disclosed in patent application EP 3 615 111 A1, filed by the same applicant as the present invention, the content of which is incorporated herein in its entirety.

In order to achieve a sufficiently homogenous and fine mist of liquid droplets, usually, relatively high pressures such as 10 bar or up to 100 or even up to 1000 bar, are necessary. To keep the amount of vaporized liquid for each dose acceptably low, the nebulizing nozzle comprises usually one or several channels, each having a cross section only in the order of several $\mu m^2$, e.g. from 2 $\mu m^2$ to 200 $\mu m^2$. The channels are present in a nozzle body and are often fabricated using micro technological fabrication techniques such as micro etching, micro lithography, and the like.

However, these techniques are often targeted at hard and brittle materials such as silicon, glass or metal, and in order to avoid any undesired deformation of the nozzle body when being subjected to said high pressures, the nozzle body is often made from a very rigid material. However, this delicate and essential element of the entire device must be securely be fixed within the same. This involves liquid tightness as well as mechanical safety. Therefore, the fixture of said nozzle body within the inhalation device demands special attention.

From document EP 0 853 498 B1, a nozzle fixture is known which comprises a pot shaped holder with a recess inside, and an elastomeric molding configured to fit into this recess. The molding itself has an opening designed to receive the nozzle body. When inserted into the recess, one of the surfaces of the molding (and the nozzle body) is exposed to the high pressure during use. The holder has a small orifice in its bottom which aligns with the nozzle outlet, and the matching walls of both the holder and the molding are frustum shaped.

According to more recent document DE 10 2004 001 451 A1, the aforementioned solution works well for medium and high pressures but provides insufficient tightness for low pressures of e.g., less than 10 bar. Therefore, the latter document proposes a solution where said holder is complemented at the high pressure side with a counterpart closing the holder, said counterpart having a circumferential ridge, said ridge being designed to displace elastic material of said molding when being pressed against the same when assembled. Further, on its high-pressure side, the molding is not flat, but has centrally a sloping recess, resulting in slants or chamfers which are inclined towards the centrally arranged nozzle body.

Likewise, WO 03/097139 A1 discloses a nozzle system for a liquid-dispensing device, comprising a nozzle and a device fixing the nozzle in the dispensing device. The nozzle-fixing device can be fixed by a second fixing device e.g., in the form of a cap nut. The side of the fixing device is which faces the outlet of the nozzle is provided with a specific geometry minimizing the portion of dispensed liquid that is deposited on the fixing device.

WO 2019/102002 A1 discloses a nozzle fixing assembly for an inhalation device comprising an elastically deformable seal element having a continuous opening capable of receiving a nozzle body. The high-pressure side of said seal element is substantially flat and the high-pressure side of said seal element is chamfered in a way that, in the partially assembled state, the distance between these high-pressure sides is higher in a central region than in a peripheral region.

While the latter solution was claimed to result in an increased liquid tightness also at low pressures, the elastomeric deformable seal on its high-pressure side is exposed to the liquid to be nebulized which has been proven disadvantageous, especially with regard to specific combinations of elastic sealing material and liquid to be nebulized.

The object of the invention is to provide a device that avoids the drawbacks of the known art. In particular, the nozzle fixture should provide a sufficient liquid tightness within the entire typical pressure range of an inhalation device, and its parts should be easy to manufacture and to assemble. Furthermore, the direct contact between the elastomeric sealing material and the liquid to be nebulized should be minimized.

SUMMARY OF THE INVENTION

In a first aspect, the invention relates to a device (10) for clamping a fluidic component (20) which is subjected to a fluctuating fluid pressure, said fluidic component (20) having a downstream end (21), an opposite upstream end (22) and an outer contour (23), said device comprising
  a holder (30) having an downstream end (31) and an opposite upstream end (32) and an inner contour (33), wherein in the partially assembled state the fluidic component is arranged inside the holder and wherein the downstream end (21) of the fluidic component (20) is supported by the downstream end (31) of the holder,
  an elastomeric shaped part (40) having an downstream end (41) and an opposite upstream end (42) and an inner contour (43) and an outer contour (44), wherein the inner contour (43) of the elastomeric shaped part (40) encloses and contacts the outer contour (23) of the fluidic component, and a mating part (50) adapted to be secured to the upstream end (32) of the holder (30), wherein the mating part has an downstream end (51) and an opposite upstream end (52) and an outer contour (53), wherein the outer contour (52) of the mating part is adapted to the inner contour (33) of the holder, and wherein the mating part comprises at least one projection (55), and wherein the projection projects into the holder and contacts and deforms the elastomeric shaped part, wherein the elastomeric shaped part comprises at least one compensating surface (45), and wherein the at least one compensating surface (45) in the partially assembled state does not contact the mating part or the at least one projection of the mating part.

In a second aspect, the present invention provides for a fluidic assembly such as a nozzle assembly comprising the device for clamping a fluidic component such as a nozzle according to the first aspect of the invention and a fluidic component, specifically a nozzle, clamped by the device.

In a third aspect, the present invention provides for an inhalation device for the inhalative administration of a medically active liquid in nebulized form, wherein the inhalation device comprises a device according to the first aspect of the invention or, more specifically, a fluidic assembly according to the second aspect of the invention.

In a fourth aspect, the invention provides for a method for clamping a fluidic component, specifically a nozzle such as an impingement-type nozzle, or, in other words, a method for the preparation of a fluidic assembly according to the second aspect of the invention, the method comprising the steps of a) providing the components of a device for clamping a fluidic component according to the first aspect of the invention, comprising
  a holder;
  an elastomeric shaped part having at least one compensation surface;
  a fluidic component, specifically a nozzle, such as an impingement-type nozzle; and
  a mating part comprising at least one projection;

b) assembling the device by
  b1) introducing the elastomeric shaped part into the holder and, subsequently, introducing the fluidic component into the elastomeric shaped part, or
  b2) introducing the fluidic component into the elastomeric shaped part and, subsequently, introducing the elastomeric shaped part holding the fluidic component into the holder; and c) securing the mating part to the holder and thereby compressing the elastomeric shaped part by contacting the at least one protrusion of the mating part with the (upstream surface) of the elastomeric shaped part.

DETAILED DESCRIPTION OF THE INVENTION

Figures 1, 2:
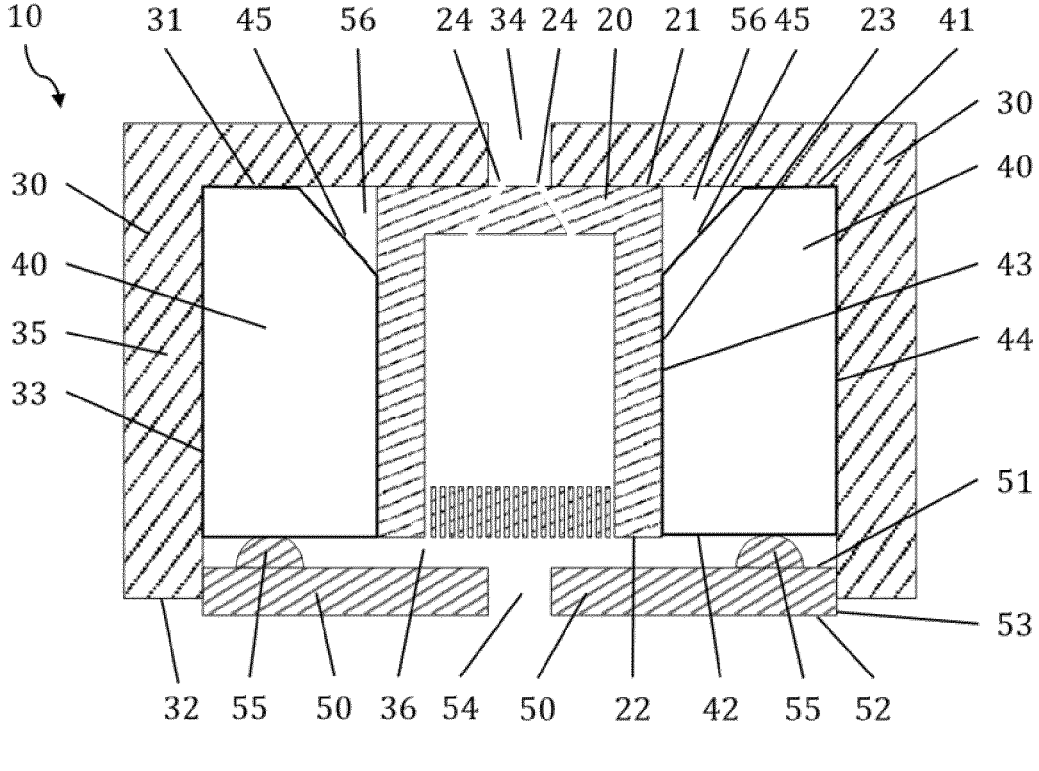
FIG. 1 depicts a device for clamping a fluidic component with an elastomeric shaped part having a compensating surface facing the fluidic component and a fluidic component introduced into the elastomeric shaped part prior to final assembly.
FIG. 2 shows the device of FIG. 1 as well as a fluidic assembly according to the present invention in the assembled state.

In a first aspect, the present invention provides for a device for clamping a fluidic component which is subjected to a fluctuating fluid pressure, said fluidic component having a downstream end, an opposite upstream end and an outer contour, said device comprising a holder having a downstream end and an opposite upstream end and an inner contour, wherein in the partially assembled state the fluidic component is arranged inside the holder and wherein the downstream end of the fluidic component is supported by the downstream end of the holder, an elastomeric shaped part having a downstream end and an opposite upstream end and an inner contour and an outer contour, wherein the inner contour of the elastomeric shaped part encloses and contacts the outer contour of the fluidic component, and a mating part adapted to be secured to the upstream end of the holder, wherein the mating part has an downstream end and an opposite upstream end and an outer contour, wherein the outer contour of the mating part is adapted to the inner contour of the holder, and wherein the mating part comprises at least one projection, and wherein the projection projects into the holder and contacts and deforms the elastomeric shaped part (in the assembled state), wherein the elastomeric shaped part comprises at least one compensating surface, and wherein the at least one compensating surface in the partially assembled state does not contact the mating part or the at least one projection of the mating part.

In an alternative description, according to this first aspect, the invention provides for a device for clamping a fluidic component which is subjected to a fluctuating fluid pressure, said fluidic component having a downstream end, an opposite upstream end and an outer contour, said device comprising a holder having a downstream end and an opposite upstream end and an inner contour, wherein in the partially assembled state the fluidic component is arranged inside the holder and wherein the downstream end of the fluidic component is supported by the downstream end of the holder, an elastomeric shaped part having a downstream end and an opposite upstream end and an inner contour and an outer contour, wherein the inner contour of the elastomeric shaped part encloses and contacts the outer contour of the fluidic component, and a mating part adapted to be secured to the upstream end of the holder, wherein the mating part has an downstream end and an opposite upstream end and an outer contour, wherein the outer contour of the mating part is adapted to the inner contour of the holder, and wherein the mating part comprises at least one projection, and wherein the projection projects into the holder and contacts and deforms the elastomeric shaped part (in the assembled state), wherein the elastomeric shaped part comprises at least one compensating surface, and wherein the at least one compensating surface is located at the downstream end of the elastomeric shaped part or in the interior of the elastomeric shaped part.

In other words, in this alternative description the first aspect of the invention relates to a device as defined above, wherein the at least one compensating surface is not located at the upstream end of the elastomeric shaped part.

The device according to this first aspect of the invention (hereinafter also referred to as "clamping device") is suitable for clamping or, in other words, securing or securely holding a fluidic component. The term "fluidic component" as used herein may be understood in a broad sense as a component that may be used or incorporated in a fluidic device for the delivery, administration or conveyance of a fluid or liquid, especially a fluidic device for medical purposes such as in a pump for medically active liquids or fluids, inhalation devices nebulizers and the like. In the context of the present invention, preferred fluidic components are components for inhalation devices, specifically nebulizers for the aerosolization and administration of medically active liquids in nebulized or aerosolized form. In specific embodiments, such nebulizers may comprise micro-engineered parts such as nozzles for the nebulization or aerosolization of a liquid.

Accordingly, in specific embodiments of the present device, the fluidic component is a nozzle for nebulization or aerosolization of a liquid. In further specific embodiments the fluidic component is a nozzle for nebulization or aerosolization (as used herein synonymously) of a medically active liquid to be administered to a subject in need thereof by inhalation as described in further detail below. In further specific embodiments, the fluidic component or, more specifically, the nozzle may be of a type that is used in so-called soft mist inhalers (SMIs), and configured to emit at least two jets of liquid to be nebulized such as to collide and form an aerosol of dispersed liquid droplets in air. Such impingement-type nozzles are adapted to function at relatively high pressure, such as in the range from about 10 bar to about 100 bar or even up to about 300 bar, whereas the pressures typically are generated by a pumping unit instead of a pressurized gas or other propellant. An example of an inhalation device of that type is described in WO 2018/197730 A1 the entire contents of which are incorporated herein by reference. Accordingly, in specific embodiments, the fluidic component to be clamped or secured by the device of the present invention is an impingement-type nozzle.

The fluidic component to be clamped or secured by the device of the present invention, in specific embodiments, may be micro-engineered or miniaturized component and, accordingly, may have small outer dimensions, typically within the range of several centimeters to 1 mm or even below. Typical dimensions for a nozzle, specifically for an impingement-type nozzle as described above, accordingly range from about 2 mm to about 20 mm with regard to the longest side of a cuboid structure, for example. The fluidic components to be clamped or secured by the device of the present invention may have various shapes, such as cylindrical or rectangular shape or the shape of a truncated cone. In specific embodiments, however, the fluidic component has a cylindrical or rectangular shape. The fluidic component, specifically the nozzle or impingement-type nozzle as described above to be clamped by the clamping device of the present invention, are usually manufactured from a hard, wear-resistant and in specific cases brittle material, such as glass or silicon.

Due to the miniaturized dimension, it may also be possible that not only a single, but also a plurality of fluidic components as described above may be clamped or secured by the device of the present invention. In that regard, the term "a fluidic component" as used herein also refers to a single fluidic component of a plurality of identical or different fluidic components. Accordingly, in specific embodiments the device of the present invention is adapted for clamping a plurality of components, such as 2 to 4 components, or 2 or 3 components, specifically 2 components.

The fluidic component to be clamped by the device of the present invention, under normal circumstances, is subjected to a fluctuating fluid pressure or even a sharply fluctuating fluid pressure, such as a high-pressure phase in which pressures of up to 200 bar and more are applied to the fluidic component, specifically the nozzle, immediately followed by a sharp decrease in pressure, for example when the liquid or fluid to be dispensed by the fluidic component is ejected from the nozzle. In general, however, the term "fluctuating fluid pressure" as used herein is to understood in a broad sense as meaning that the pressure exerted on the fluidic component is not constant and varies (increases or reduces) in the course of time either continuously or discontinuously, whereas the pressure change can be a single event or can be applied to the fluidic component repeatedly, such as it is the case for a nozzle in an inhaler device as described above.

The device according to the invention, preferably is adapted to be substantially pressure- and liquid tight, which means that during normal use, despite the usually high pressures that may be applied to the fluidic component such as a nozzle, no, or only a very small neglectable leakage is desired. In particular, the device is adapted to be pressure- and liquid tight, when a fluidic component such as a nozzle body is inserted, i.e. when the device is in the partially assembled state as described in further detail below.

The fluidic component to be clamped or secured by the device of the present invention has a downstream end and an opposite upstream end. The terms "downstream" or "upstream" as used herein in connection with various components of the present device are to be understood as defining opposing sides or ends of the respective component relative to the direction in which a fluid or liquid is delivered or conveyed in connection with the fluidic component, whereas "downstream" denotes the side or direction in which the fluid or liquid is delivered and "upstream" denotes the side or direction from which the fluid or liquid is delivered.

In cases in which the fluidic component is a nozzle as described above, the upstream side or end of the nozzle is, in order to nebulize the fluid or liquid, subjected to a high pressure of liquid and accordingly, may also be referred to as "high-pressure" side. The liquid to be aerosolized or nebulized is usually pressed into one or several channels, such as inlet channels, optionally comprising filters or the like. The opposite end of the channel(s) ends in the actual nozzle outlet, where an inhalable mist is produced upon actuation of the device. As this downstream end is surrounded by ambient pressure it may also be referred to as "low-pressure" side.

Furthermore, the fluidic component has an outer contour or surface which may be understood as the outer surface or sidewalls of the fluidic component extending between the upstream end and the opposite downstream end of the fluidic component. Depending on the general design and outer shape of the fluidic component as described above, the contour may be in general circular or elliptic (e.g. when the fluidic component has the shape of a cylinder or truncated cone) or it may have a plurality of substantially flat sidewalls (e.g. when the fluidic component has a rectangular or polygonal shape. In specific embodiments, the fluidic component has a cylindrical or rectangular shape. Furthermore, the contour or outer surface of the fluidic component may have irregular shapes such as star-like shapes.

The device of the present invention further comprises a holder having a downstream end and an opposite upstream end (as defined above in connection with the fluidic component). The holder, furthermore, has an inner contour or inner surface which is to be understood as the inner contour or surface of the sidewall of the holder extending from the downstream end to the upstream end of the holder. In specific embodiments, especially in cases in which the present clamping device is to be implemented in an inhaler device such as a hand-held inhaler device, the holder may have an outlet opening located at the downstream end through which the liquid or fluid to be dispensed may be ejected. In general, the holder may have various outer shapes such as an overall rectangular, cylindrical, polygonal or irregular shape whereas the upstream end of the holder preferably is open resulting in an overall cup- or bowl-like shape to allow for the introduction of further components such as the fluidic component or the elastomeric shaped part or the mating part as described below. In specific embodiments, the holder is open or, other words, has an access opening over the entire inner diameter at its upstream end or side, thereby allowing access to the inner lumen of the holder. Accordingly, the fluidic component as well as the further components of the present device may be inserted into the holder via the access opening.

In the partially assembled state, the fluidic component is arranged inside the holder in a way that the downstream end of the fluidic component is supported by the downstream end of the holder. In specific embodiments, especially in cases in which the fluidic component is a nozzle to be secured within an inhalation device, the fluidic component may be arranged within the holder such that the ejection channels of the nozzle are co-located with the outlet opening of the holder to allow for the ejection and nebulization of the liquid. The term "supported by the downstream end of the holder" in connection with the fluidic component means that the fluidic component may directly contact (the inner contour or surface) of the downstream end of the holder or may indirectly contact the holder, e.g. via an additional seal or other connecting and/or buffering structure located between the fluidic component and (the inner contour) of the downstream end of the holder. In specific embodiments, the holder may comprise means for establishing a connection to the mating part as described in further detail below, e.g. by establishing a form-fit or force-fit connection such as a snap-fit connection or by a screw thread, whereas such means may be preferably located at the upstream end of the holder.

The device of the present invention further comprises an elastomeric shaped part having a downstream end and an opposite upstream end (as defined above in connection with the fluidic component). The elastomeric shaped part may have a generally ring-like shape with an inner opening in which the fluidic component may be received and, after final assembly of the present device, may be clamped or secured. The outer surface or contour of the elastomeric shaped part, in general, may be adapted to the inner contour of the holder and, more specifically has a size and shape that it fits into the inner lumen of the holder, both, prior to assembly as well as in the partially assembled state of the device as described in further detail below. Accordingly, in specific embodiments, the overall volume of the elastomeric shaped part equals or is smaller than the overall volume of the inner lumen of the holder. Due to its generally ring-like shape, the elastomeric shaped part has an inner contour or surface which, after insertion of the fluidic component, encloses and contacts the outer contour of the fluidic component, preferably over the entire circumference of the fluidic component, after assembly or final assembly of the present device. Before assembly, however, the cross section of the inner opening of the elastomeric shaped part may be slightly larger than the cross-section of the fluidic component to be enclosed or secured. For example, the cross-sectional diameter of the inner opening may be from about 10 μm to about 2 mm or to about 1 mm larger than the corresponding cross-sectional diameter of the fluidic component.

As described in more detail below, however, the outer surface or contour of the fluidic component may or may not entirely be in contact with the inner contour of the elastomeric shaped part, especially prior to final assembly of the present device or fluidic assembly. In specific embodiments, the entire outer contour (corresponding to the surface of the sidewalls of the fluidic component) of the fluidic component contacts the inner contour of the elastomeric shaped part. In alternative embodiments, however, only from about 50% to about 99%, or from about 60% to about 95%, or from about 70% to about 90% of the outer contour or surface of the fluidic component contacts the inner surface of the elastomeric shaped part when the fluidic component is introduced into the elastomeric shaped part, however, before the device is assembled as described in detail below.

In specific embodiments, the elastomeric shaped part is made of an elastically deformable material which can be deformed when subject to external pressure applied to an outer surface of the elastomeric shaped part, such as the deforming pressure exerted by the at least one projection of the mating part as described in further detail below. In further specific embodiments, the elastomeric shaped part is made of a material with a low compressibility which allows for the transfer of the applied pressure to one side or surface of the elastomeric shaped part to another or other surfaces thereof. In other words, depending on the compressibility of the elastomeric shaped part, the deformation of one surface or side of the elastomeric shaped part results in the dilation of another surface or side of the same element, preferably in the dilatation of at least one compensating surface as described in further detail below.

Accordingly, the elastomeric shaped part may comprise or essentially consist of a broad variety of elastomeric materials such as synthetic rubbers such as fluoropolymeric materials, e.g. Viton®, nitrile butadiene rubber (NBR), ethylene propylene diene monomer rubber (EPDM), poly-tetrafluoroethylene (PTFE), silicone or liquid silicone rubber (LSR).

The device according to the present invention further comprises a mating part which is adapted to be secured to the upstream end of the holder and, in specific embodiments, is secured to the upstream end of the holder in the assembled state of the present device. The mating part has a down-stream end and an opposite upstream end and an outer contour or surface. The outer contour or surface of the mating part is adapted to the inner contour of the holder, specifically to the inner contour of the holder surrounding the access opening of the holder. A mentioned above, the mating part may be secured to the holder, specifically by insertion of the mating part into the access opening of the holder. In specific embodiments, the connection of the mating part to the holder may be established by a form-fit or force-fit connection, specifically by a snap-fit connection or by a screw thread whereas e.g. the mating part may be screwed into the (access opening) of the holder. Accord-ingly, the inner lumen of the holder may be closed and further reduced by securing the mating part to the holder as described above. The term "assembled state" as used herein means a state of the present clamping device in which all components of the device have been assembled and the mating part is secured to the holder, or in other words, in which the device is ready for use. The term "partially assembled state" as used herein, however, means a state of the device in which all components of the present device have been assembled and the mating part is not yet secured to the holder.

In specific embodiments, during assembly of the device according to the present invention, the elastomeric shaped part may be introduced into the holder via the access opening of the holder followed by introduction of the fluidic component into the inner opening of the elastomeric shaped part. As an alternative, the fluidic component may be inserted into the inner opening of the elastomeric shaped part followed by introduction of the assembled elastomeric shaped part and fluidic component into the inner lumen of the holder. In both cases, after introduction of the elasto-meric shaped part and the fluidic component into the holder via the access opening, the access opening may be closed by securing the mating part to the holder as described above.

The mating part, in some embodiments, may have a generally flat shape such as a rectangular or square board or round, elliptic or even irregular disk. In specific embodi-ments, however, especially when the mating part has a screw thread for establishing the connection to the holder, the mating part may have the form of a flat disk with a round circumference to fit into a corresponding round access opening of the holder. The mating part may also have a fluid opening to allow access of the fluid to be delivered or nebulized to the fluidic component such as a nozzle.

The mating part, furthermore, comprises at least one projection located on and attached to the downstream end or, more specifically, to the surface of the downstream end of the mating part. Accordingly, in the assembled state or, in other words, when the fluidic element and the elastomeric shaped part are introduced into (the inner lumen of) the holder and the mating part is secured to the holder the projection projects into the holder and contacts and deforms the elastomeric shaped part contained therein. In specific embodiments, the at least one projection contacts and deforms the upstream end of the elastomeric shaped part so that the elastomeric shaped part is deformed and/or com-pressed as described in further detail below.

The at least one projection located on the downstream surface of the mating part may, in general, have different forms or shapes suitable for the deformation and compres-sion of the elastomeric shaped part. In other words, suitable shapes for the at least one projection are mechanically sufficiently stable to compress and deform the elastomeric shaped part under the pressure exerted by the mating part when secured to the holder. Furthermore, suitable shapes of the projection allow for the effective compression and deformation of the elastomeric shaped part without, e.g. piercing into the elastomeric shaped part. In some embodi-ments, however, especially when a plurality of projections with different shapes or irregular shapes are implemented, a certain degree of piercing into the elastomeric shaped part may be advantageous to allow for the immobilization of the elastomeric shaped part. In specific embodiments, as already mentioned above the projection may be in the form of a single projection or in the form of a plurality of projections, such as from 2 to about 100 or to about 75 or to about 50 projections or 2 to 25 projections, for example 2 to about 20, or 3 to about 15, or about 4 to about 10 projections.

In case of a plurality of projections, the projections may have the same form or shape or, independently from each other, may have different forms or shapes. Suitable forms or shapes include, but are not limited to dots, rings, bars, such as parallel bars or crossed bars such as honeycomb struc-tures as well as irregular shapes, whereas the rings and bars may be continuous or discontinuous such as a plurality of bars oriented radially with regard to the central main axis of the present device. When provided in form of a ring or a plurality of rings, the rings may have a circular shape, preferably centered around a longitudinal main axis of the present device connecting the (center of) the downstream end of the device with the (center of) the upstream end of the device. In specific embodiments, the at least one projection of the mating part may have the form of at least one annular ring. In further specific embodiments a plurality of annular rings may have different diameters and may be arranged concentrically around the same center. In further embodi-ments, the at least one projection may have the form of a sinuous line, either circular, such as a collar, or non-circular.

The at least one projection of the mating part, indepen-dently of the general shape as described above with regard to the horizontal dimension, i.e. horizontal to the main axis of the device as described above, in some embodiments, may have a uniform or continuous height as measured from the downstream surface of the mating part. In further embodiments, the at least one projection may have a non-uniform height which means that in case of one projection, such as an annular ring, the projection may have a varying height or in cases of a plurality of projections the projections may have different heights as measured from the down-stream surface of the mating part.

Furthermore, the at least one projection may have differ-ent cross-sectional shapes when seen along a vertical cross-sectional plane, i.e. a plane perpendicular to the (down-stream end) of the mating part. In some embodiments, the at least one projection, for example, may a have a round shape, a pointed shape a cubic shape or the shape of a trapezoid defining a width at the upstream end of the projection (contacting the downstream surface of) the mating part and an equal or different, i.e. smaller width at the opposite downstream end. In specific embodiments, the height of the at least one projection (as measured from the downstream end of the mating part) may be in the range of from about 100 μm to about 20 mm, such as from about 500 μm to about 6 mm, or from about 500 μm to about 2 mm. In further specific embodiments, the maximum width of the at least one projection, i.e. the width at the basis of the projection facing the downstream end of the mating part may be within the range of from about 100 μm to about 20 mm, such as from about 500 μm to about 6 mm, or from about 500 μm to about 2 mm. In further specific embodiments, a plurality of projections has an equal height and/or width.

The at least one projection as defined above, accordingly may have an overall volume Vp which is to be understood as the overall inner volume of a single projection as measured from the downstream surface of the mating part or, in case of a plurality of projections the sum of the individual volumes of the plurality of projections.

The holder and, independently thereof, the mating part comprising the at least one projection may be made of a material with a sufficient mechanical stability or stiffness such as for example metals like stainless steel or thermoplastic polymers which allow for the production of the respective component by injection molding. In specific embodiments, the holder and/or the mating part and/or the at least one protrusion comprises or essentially consists of stainless steel, polyethylene, polystyrene, polyether ether ketone (PEEK), acrylonitrile butadiene styrene (ABS), polycarbonate and polyamide, particularly PEEK.

The elastomeric shaped part of the device according to the present invention comprises at least one compensating surface. The term "compensating surface" of the elastomeric shaped part as used herein defines a surface or contour of the elastomeric shaped part which, after introduction of the elastomeric shaped part and the fluidic component into the holder as described above, however before the access opening of the holder is closed by securing the mating part to the (upstream end of) the holder (i.e. in the partially assembled state), does not contact the inner surface of the holder or the outer surface of the fluidic component, thereby defining a hollow space (hereinafter referred to as "compensating volume") into which the elastomeric shaped part can expand when being compressed by the mating part and/or by the at least one projection of the mating part (in the assembled state).

In an equivalent description, a compensating surface is a surface or surface area of the elastomeric shaped part which does not contact the inner surface of the holder and/or the outer surface of the fluidic component in the partially assembled state (in which the elastomeric shaped part and the fluidic component have been introduced into the holder) and which contacts the inner surface of the holder and/or the outer surface of the fluidic component in the assembled state in which the mating part is secured to the holder, thereby deforming and compressing the elastomeric shaped part.

In yet a further equivalent description, the term "compensating surface" means a surface or surface area of the elastomeric shaped part which is deformable, more specifically expandable, upon contact and deformation of the elastomeric shaped part by the mating part (in the assembled state). As described in further detail below, however, the compensating surface does not contact the mating part or the at least one projection of the mating part.

It should be noted that a compensating surface as referred to herein allows to effectively and pressure- and liquid-tightly clamp and fix the fluidic component to be held by the elastomeric shaped part, without however, the risk of deformation or damaging of the micronized and in many cases delicate fluidic component, especially in cases in which such fluidic component is made of a brittle material, such as glass or silicon.

In specific embodiments, the compensating surface is located at the downstream (low-pressure) end of the elastomeric shaped part. In further specific embodiments, the compensating surface formed by that at least a part of the downstream surface of the elastomeric shaped part is inclined or sloped or chamfered (with regard to a plane perpendicular to the main axis of the device) towards the inner and/or the outer contour of the elastomeric shaped part.

The terms "inclined" or "sloped" or "chamfered" as used in that context mean that the distance (perpendicular to the main axis of the device) between the compensating surface and either the outer surface of the fluidic component (in case the compensating surface faces the fluidic component) or the inner surface of the holder (in case the compensating surface faces the holder), as the case may be, is larger at the downstream end side and decreases from the downstream end towards the upstream end continuously or discontinuously, e.g. linearly, after introduction of the elastomeric shaped part into the holder, however prior to securing the mating part to the holder.

Accordingly, the elastomeric shaped part may have one compensating surface or a plurality of compensating surfaces. For example, in some embodiments, the downstream surface of the elastomeric shaped part (before assembly of the device as described above) may be inclined, sloped or chamfered towards the inner contour of the elastomeric shaped part, resulting in a hollow space, i.e. a compensating volume, confined by the holder, the elastomeric shaped part and the fluidic component. In further embodiments, the downstream surface of the elastomeric shaped part (before assembly of the device as described above) may be inclined, sloped or chamfered towards the outer contour of the elastomeric shaped part, resulting in a hollow space (i.e. compensating volume) confined by the holder and the elastomeric shaped part only. In yet further specific embodiments, the downstream surface of the elastomeric shaped part (before assembly of the device) may be inclined, sloped or chamfered to towards the inner contour of the elastomeric shaped part and towards the outer contour of the elastomeric shaped part, resulting in two hollow spaces (or compensating volumes) separated from each other and confined by either the holder, the elastomeric shaped part and the fluidic component or by the elastomeric shaped part and the holder only.

The term "compensating volume" as used herein may also be understood as to refer to a hollow space defined and confined by the compensating surface of the elastomeric shaped part which, after introduction of the elastomeric shaped part and the fluidic component into the holder as described above, however before the access opening of the holder is closed by securing the mating part to the (upstream end of) the holder, does not contact the inner surface of the holder or the outer surface of the fluidic component, thereby defining a hollow space into which the elastomeric shaped part can expand when being compressed by the mating part and/or by the at least one projection of the mating part.

In further specific embodiments, the compensating surface of the elastomeric shaped part can be an internal surface formed by an inner space or volume or a plurality of inner spaces or volumes located within the elastomeric shaped part. Accordingly, in specific embodiments, the compensating surface is formed by at least one hollow space located in the interior of the elastomeric shaped part and, in specific embodiments does not have contact to the surrounding atmosphere, the outer surface of the fluidic component nor the inner surface of the holder or, in other words, is entirely surrounded by the material of the elastomeric shaped part. In these cases, the compensating volume as defined above may also be referred to as "internal compensating volume" and, correspondingly the compensating surface may be referred to as "internal compensating surface".

The internal compensating volume within the elastomeric shaped part, in some embodiments, may be a single hollow space, such as an inner channel surrounding the inner contour of the elastomeric shaped part. Accordingly, in specific embodiments, the internal compensating volume is formed by a hollow annular space located in the interior of the elastomeric shaped part.

In other specific embodiments, the internal compensating volume may be in the form of a plurality of discrete hollow spaces, e.g. spherical or ellipsoid hollow spaces distributed within the elastomeric shaped part or aligned, e.g. along a perimeter surrounding the inner contour of the elastomeric shaped part.

In further specific embodiments, the internal compensating volume or plurality of volumes may have one or a plurality of channels connecting the internal compensating volume to the surrounding atmosphere to provide for a pressure compensation within the internal compensating volume(s).

It should be noted that in cases in which the compensating surface is an internal compensating surface, the outer contour or surface of the elastomeric shaped part may be shaped to completely fill the inner volume of the holder so that, in other words, no (external) compensating surface is necessary. In other embodiments, however, it may be advantageous to combine at least one (external) compensating surface with at least one internal compensating surface.

As described above for the at least one projection, the compensating volume or internal compensating volume as defined above, may have an overall volume Vc which is to be understood as the overall inner volume of a single compensating volume or in internal compensating volume or, in case of a plurality of compensating volumes and/or internal compensating volumes, the sum of the individual volumes of the plurality of internal compensating volumes. In typical cases, the overall volume Vc may be selected within a range of from about 5% to about 80%, or from about 15% to about 30% of the total volume of the elastomeric shaped part.

According to the present invention, the at least one compensating surface (in the fully assembled state of the device or, in other words, in the fluidic assembly according to the present invention) does not contact the mating part and/or the at least one projection of the mating part. In other words, as described above, the at least one compensating surface is located at the downstream end of the elastomeric shaped part or in the interior of the elastomeric shaped part.

In specific embodiments, the at least one compensating volume or surface does not contact the mating part and the at least one projection of the mating part, preferably, in the case of a plurality of projections, all of the plurality of projections. In other embodiments, the at least one compensating volume or surface does not contact the mating part or the at least one projection of the mating part, preferably, in the case of a plurality of projections, all of the plurality of projections.

In other words, when the elastomeric shaped part as well as the fluidic component contained therein are introduced into the holder, the holder may be closed and the device of the present invention or, more specifically the fluidic assembly comprising the device as well as the fluidic component, may thereby be completed by attaching or securing the mating part to the holder without the mating part and/or the at least one projection contacting any of the compensating surface or volume of the elastomeric shaped part. As also described above, the at least one projection of the mating part projects into the holder and contacts the (upstream surface) of the elastomeric shaped part. While attaching or securing the mating part to the holder, the at least one projection of the mating part compresses the elastomeric shaped part so that the fluidic element enclosed by (the inner surface of) the elastomeric shaped part is securely clamped and fixed in the elastomeric shaped part and the compensation surface are deformed so that the corresponding compensating volumes are reduced or completely filled.

It has surprisingly found, however, that the fluidic component may be effectively fixed without the risk of damaging or deforming the fluidic component when the compensating volume or surface is not located at the upstream end of the elastomeric shaped part. Accordingly, in specific embodiments of the present device, the compensating surface of the elastomeric shaped part is not located at the upstream end of the elastomeric shaped part.

As already described above, the compensating surface may be located at the downstream end of the elastomeric shaped part and may be formed by that at least a part of the downstream surface of the elastomeric shaped part is inclined or sloped or chamfered (with regard to a plane perpendicular to the main axis of the device) towards the inner and/or the outer contour of the elastomeric shaped part. In other embodiments, as also described above, a compensating surface may be defined by a hollow space within the elastomeric shaped part (as an internal compensating surface). In both cases, the at least one compensating surface of the elastomeric shaped part provides for a space or compensating volume into which the elastomeric shaped part can expand when being compressed by the mating part and/or by the at least one projection of the mating part.

In specific embodiments, the surface, or more specifically, the entire surface of the upstream end of the elastomeric shaped part contacts the downstream surface of the mating part and/or of the at least one projection. However, as no compensating surface or volume is located at the upstream end of the elastomeric shaped part, the mating part, or more specifically, the downstream surface of the mating part and/or the at least one projection located thereon does not contact said compensating area or surface.

In further specific embodiments in which the elastomeric shaped part comprises a compensating surface and optionally an additional internal compensating surface as defined above, all other outer surfaces of the elastomeric shaped part are enclosed by and in contact with the inner surfaces of the holder or the mating part. In yet further specific embodiments in which the elastomeric shaped part comprises an internal compensating surface as defined above only, all outer surfaces of the elastomeric shaped part are enclosed by and in contact with the inner surfaces of the holder or the mating part.

Independent of the specific location of the compensating surface(s) as described above according to the present invention, the internal pressure generated within the elastomeric shaped part when compressed by the at least one protrusion of the mating part can effectively and evenly be distributed over the entire elastomeric shaped part by allowing the elastomeric shaped part to expand into a compensation volume or internal compensating volume generated by the compensation surface or an inner compensating surface which is not in contact with the mating part or the at least one protrusion and, in other words, is located remote from the upstream surface of the elastomeric shaped part deformed by the mating part or the at least one protrusion thereof.

In further specific embodiments of the device according to the present invention, the at least one projection has an overall volume Vp and the compensating volume or internal compensating volume has an overall volume Vc, and wherein the overall volume Vp of the at least projection is adapted to the overall volume Vc of the compensating volume or internal compensating volume. In further specific embodiments, the overall volume Vp of the at least projection (the sum thereof) amounts to at least about 10%, such as from about 10% to about 50%, or from about 20% to about 30% of the overall compensating volume Vc.

As described above, the device according to the present invention allows for the effective clamping of a fluidic component, especially of a nozzle to be securely, pressure- and liquid-tightly and precisely clamped or secured in an inhalation device, especially in cases in which the inhalation device is a hand-held device and the fluidic component is a miniaturized multi-channel impingement type nozzle to be clamped and secured within a soft-mist inhalation device which is operated with high fluid pressures of at least 10 bars, often at fluid pressures within the range of from about 50 to about 250 bar. Surprisingly, it has been found that a fluidic component such as a miniaturized nozzle may be affectively clamped by an elastomeric shaped part when neither the mating part nor the protrusions are in direct contact with the compensating surfaces and that this design, especially in cases in which the fluidic component is to be assembled with or introduced to the elastomeric shaped part prior to insertion into the holder, this has been proven beneficial for the assembly process with regard to delicate fluidic components such as a nozzle.

In a further aspect, the present invention provides for a fluidic assembly such as a nozzle assembly comprising the device for clamping a fluidic component such as a nozzle according to the first aspect of the invention as described in detail above and a fluidic component, specifically a nozzle, clamped by the device.

Accordingly, the present invention provides for a fluidic assembly comprising a device for clamping a fluidic component which is subjected to a fluctuating fluid pressure, said fluidic component having a downstream end, an opposite upstream end and an outer contour, said device comprising a holder having a downstream end and an opposite upstream end and an inner contour, wherein in the partially assembled state the fluidic component is arranged inside the holder and wherein the downstream end of the fluidic component is supported by the downstream end of the holder, an elastomeric shaped part having a downstream end and an opposite upstream end and an inner contour and an outer contour, wherein the inner contour of the elastomeric shaped part encloses and contacts the outer contour of the fluidic component, and a mating part adapted to be secured to the upstream end of the holder, wherein the mating part has an downstream end and an opposite upstream end and an outer contour, wherein the outer contour of the mating part is adapted to the inner contour of the holder, and wherein the mating part comprises at least one projection, and wherein the projection projects into the holder and contacts and deforms the elastomeric shaped part (in the assembled state), wherein the elastomeric shaped part comprises at least one compensating surface, and wherein the at least one compensating surface in the partially assembled state does not contact the mating part or the at least one projection of the mating part; and a fluidic component such as a nozzle clamped by the clamping device.

It should be noted that all definitions, features, embodiments and combinations thereof as described above in connection with the device of the first aspect of the present invention (or the alternative to the first aspect of the invention) apply to the fluidic assembly of the second aspect as well as of all further aspects, accordingly.

In specific embodiments, the fluidic assembly of this aspect of this invention corresponds to the device for clamping a fluidic component such as a nozzle according to the first aspect of the invention and a fluidic component, specifically a nozzle, clamped by the device and, accordingly, corresponds to the device according to the first aspect of the invention in the assembled state as described above. In further specific embodiments, the present fluidic assembly may be a nozzle assembly comprising a nozzle holder in the form of a device according to the first aspect of the invention with a nozzle secure clamped therein. Such a nozzle assembly may be advantageously incorporated in an inhalation device, such as an inhalation device for the administration of medically active liquids in which typically nozzle structures are provided which are subject to sharply fluctuating pressures.

Accordingly, in a further aspect the present invention provides for an inhalation device for the inhalative administration of a medically active liquid in nebulized form, wherein the inhalation device comprises a device according to the first aspect of the invention, or, more specifically, a fluidic assembly or nozzle holder according to the second aspect of the invention.

In specific embodiments, the inhalation device of this aspect of the invention may be a hand-held inhalation device, specifically a soft-mist inhaler (SMI) comprising an impingement type nozzle with at least two channels through which two jets of a medically active liquid are ejected wherein the trajectories of the at least two channels intersect such that the medically active liquid when ejected at high pressures is nebulized at the point of intersection.

In yet a further aspect, the present invention provides for a method for clamping a fluidic component, specifically a nozzle such as an impingement-type nozzle, or, in other words, for the preparation or manufacture of a fluidic assembly according to the second aspect of the invention, the method comprising the steps of a) providing the components of a device for clamping a fluidic component as described above in connection with the first aspect of the invention comprising
a holder;
an elastomeric shaped part having at least one compensation surface;
a fluidic component, specifically a nozzle, such as an impingement-type nozzle; and
a mating part comprising at least one projection;

b) assembling the device by
b1) introducing the elastomeric shaped part into the holder and, subsequently, introducing the fluidic component into the elastomeric shaped part, or
b2) introducing the fluidic component into the elastomeric shaped part and, subsequently, introducing the elastomeric shaped part holding the fluidic component into the holder; and c) securing the mating part to the holder and thereby compressing the elastomeric shaped part by contacting the at least one protrusion of the mating part with the (upstream surface) of the elastomeric shaped part.

As described above, the method according to this aspect of the present invention as well as the device of the first aspect of the invention allow for the advantageous assembly of the clamping device, more specifically of the fluidic assembly of the present invention in which the clamping forces necessary to secure the fluidic component are evenly distributed within the elastomeric shaped part and accordingly allow for the liquid- and pressure-tight clamping of the fluidic component while minimizing the mechanical stress on the (potentially brittle and delicate) fluidic component.

The following is a list of numbered items which are embodiments comprised by the present invention:

1. Device (10) for clamping a fluidic component (20) which is subjected to a fluctuating fluid pressure, said fluidic component (20) having a downstream end (21), an opposite upstream end (22) and an outer contour (23), said device comprising a holder (30) having an downstream end (31) and an opposite upstream end (32) and an inner contour (33), wherein in the partially assembled state the fluidic component is arranged inside the holder and wherein the downstream end (21) of the fluidic component (20) is supported by the downstream end (31) of the holder, an elastomeric shaped part (40) having an downstream end (41) and an opposite upstream end (42) and an inner contour (43) and an outer contour (44), wherein the inner contour (43) of the elastomeric shaped part (40) encloses and contacts the outer contour (23) of the fluidic component, and a mating part (50) adapted to be secured to the upstream end (32) of the holder (30), wherein the mating part has an downstream end (51) and an opposite upstream end (52) and an outer contour (53), wherein the outer contour (52) of the mating part is adapted to the inner contour (33) of the holder, and wherein the mating part comprises at least one projection (55), and wherein the projection projects into the holder and contacts and deforms the elastomeric shaped part, wherein the elastomeric shaped part comprises at least one compensating surface (45), and wherein the at least one compensating surface (45) in the partially assembled state does not contact the mating part or the at least one projection of the mating part.

2. Device according to item 1, wherein the compensating surface is located at the downstream end of the elastomeric shaped part or in the interior of the elastomeric shaped part.

3. Device according to item 1 or 2, wherein the compensating surface is not located at the upstream end of the elastomeric shaped part.

4. Device according to any one of the preceding items, wherein the compensating surface is formed by that at least a part of the downstream surface of the elastomeric shaped part is inclined or sloped (with regard to a plane perpendicular to the main axis of the device) towards the inner and/or the outer contour of the elastomeric shaped part.

5. Device according to any one of the preceding items, wherein the compensating surface is formed by that at least a part of the downstream (low-pressure) surface of the elastomeric shaped part is inclined or sloped (with regard to a plane perpendicular to the main axis of the device) towards the inner contour of the elastomeric shaped part.

6. Device according to any one of the preceding items, wherein the compensating surface (45) is formed by at least one hollow space located in the interior of the elastomeric shaped part (40).

7. Device according to item 6, wherein the compensating surface (45) is formed by a hollow annular space located in the interior of the elastomeric shaped part (40).

8. Device according to any one of the preceding items, wherein the at least one projection (55) of the mating part (50) has the form of at least one annular ring.

9. Device according to any one of the preceding items, wherein the at least one projection (55) of the mating part (50) is in the form of a plurality of projections.

10. Device according to item 9, wherein the plurality of projections (55) has an equal height and/or width.

11. Device according to any one of the preceding items, wherein the at least one projection (55) has an overall volume Vp and wherein the compensating volume (56) or internal compensating volume has an overall volume Vc, and wherein the overall volume Vp of the at least projection (55) is adapted to the overall volume Vc of the compensating volume (56) or internal compensating volume.

12. Device according to item 11, wherein the overall volume Vp of the at least projection (55) amounts to from about 10% to about 50% of the overall compensating volume Vc.

13. Device according to any one of the preceding items, wherein the entire surface of the upstream end (42) of the elastomeric shaped part (40) contacts the downstream surface (51) of the mating part (50) and/or of the at least one projection (55).

14. Device according to any one of the preceding items, wherein the fluidic component (20) is a nozzle for nebulization or aerosolization of a liquid.

15. Device according to any one of the preceding items, wherein the fluidic component (20) is a nozzle for nebulization aerosolization of a medically active liquid to be administered to a subject in need thereof by inhalation.

16. Device according to any one of the preceding items, wherein the fluidic component (20) is an impingement-type nozzle.

17. Device according to any one of the preceding items, wherein the fluidic component (20) has a cylindrical or rectangular shape.

18. Device according to any one of the preceding items, wherein the device is adapted for clamping a plurality of fluidic components (20), preferably 2 fluidic components (20).

19. Device according to any one of the preceding items, wherein the elastomeric shaped part (40) comprises or essentially consists of synthetic rubbers, fluoropolymeric materials, nitrile butadiene rubber (NBR), ethylene propylene diene monomer rubber (EPDM), polytetrafluorethylene (PTFE), silicone or liquid silicone rubber (LSR).

20. Device according to any one of the preceding items, wherein the holder (30) and/or the mating part (50) and/or the at least one protrusion (55) comprises or essentially consists of stainless steel, polyethylene, polystyrene, polyether ether ketone (PEEK), acryloni-
trile butadiene styrene (ABS), polycarbonate and poly-
amide.

21. An inhalation device (60) for the inhalative adminis-
tration of a medically active liquid in nebulized form,
wherein the inhalation device (60) comprises a device
according to any one of items 1 to 20.

22. A method for clamping a fluidic component, the
method comprising the steps of
a) providing the components of a device for clamping
a fluidic component (20) according to any one of
items 1 to 20, comprising
a holder (30);
an elastomeric shaped part (40) having at least one
compensating surface (45);
-a fluidic component (20), specifically a nozzle, such
as an impingement-type nozzle; and
a mating part (50) comprising at least one projection
(55);
b) assembling the device by
b1) introducing the elastomeric shaped part (40) into
the holder (30) and, subsequently, introducing the
fluidic component (20) into the holder (30), or
b2) introducing the fluidic component (20) into the
elastomeric shaped part (40) and, subsequently,
introducing the elastomeric shaped part (40) holding
the fluidic component (20) into the holder (30); and
c) securing the mating part (50) to the holder (30) and
thereby compressing the elastomeric shaped part
(40) by contacting the at least one protrusion (55) of
the mating part (50) with the (upstream surface) of
the elastomeric shaped part (40).

DETAILED DESCRIPTION OF THE DRAWINGS

FIG. 1 depicts a cross-sectional view of a device 10 for
clamping a fluidic component 20 with an elastomeric shaped
part 40 having a compensating surface 45 facing a fluidic
component 20 prior to final assembly. In the embodiment
shown in FIG. 1 as well as the following Figures, the fluidic
component has the form of a nozzle, more specifically of an
impingement-type nozzle having at least two ejection chan-
nels 24 (two ejection channels depicted) as well as a
downstream end 21, an opposite upstream end 22 and an
outer contour or surface 23. As already described in detail
above, the device 10 allows for pressure- and liquid-tightly
clamping and fixing the fluidic component such as a nozzle
20 even under fluctuating fluid pressure. In FIG. 1, the
device of the present invention is shown in a state in which
it is not finally assembled and, accordingly, in which the
fluidic component is not (yet) pressure- and liquid-tightly
clamped and fixed.

The device 10 further comprises a holder 30 having a
downstream end 31 and an opposite upstream end 32 and an
inner contour or surface 33 corresponding to the inner
surface of the sidewall 35 of the holder 30. The holder
further comprises an outlet opening 34 through which,
especially in cases in which a liquid or fluid is to be
nebulized by a nozzle as the fluidic component, said liquid
or fluid may be delivered. Opposite of said outlet opening 34
the holder 30 as shown in FIG. 1 has an access opening 36
located at the upstream end 32 of the holder 30 through
which further components of the present device 10, such as
the fluidic component 20 and the elastomeric shaped part 40
as described below can be introduced into holder 30.

As shown in FIG. 1, the fluidic component 20 is arranged
inside the holder 30 and the downstream end 21 of the fluidic
component 20 is supported by the downstream end 31 of the
holder 30.

The device 10 of the present invention further comprises
an elastomeric shaped part 40 having a downstream end 41
and an opposite upstream end 42 as well as an inner contour
43 and an outer contour 44. As can be seen in FIG. 1, the
inner contour 43 of the elastomeric shaped part 40 encloses
and contacts the outer contour 23 of the fluidic component
20. It should be noted, however, that in the embodiment as
shown in FIG. 1 the inner contour 43 of the elastomeric
shaped part does not contact the entire outer contour 23 of
the fluidic component 20. As FIG. 1 provides a cross-
sectional view of device 10 which may have e.g., an overall
cubic or round shape as already mentioned above, elasto-
meric shaped part 40, although depicted as two separate,
mirror-symmetrical units in FIG. 1 and the following Fig-
ures may belong to one elastomeric shaped part 40, e.g., in
the form of a ring.

Device 10 further comprises a mating part 50 which is
adapted to be secured to the upstream end 32 of the holder
30. As shown in the embodiment of FIG. 1, the mating part
may be secured to the inner surface of the upstream end 32
of holder 30. In other embodiments, however, the mating
part may also be adapted to be secured to other areas of the
holder, such as the upstream surface of the upstream end 32
of the holder 30. As mentioned above, FIG. 1 shows a
cross-sectional view of a clamping device 10 which may
have e.g. an overall cubic or round shape. Accordingly,
holding element 50 as shown in FIG. 1 as well as the
following Figures as two separate parts actually may belong
to the same holder 30 having an overall flat circular shape
around a central main rotational axis X (see FIG. 2) of
device 10 and surrounding a fluid opening 54 through which
the fluid or liquid to be conveyed by to the fluidic component
can enter the clamping device.

The mating part 50, as well, has a downstream end or
surface 51 and an opposite upstream end or surface 52 as
well as an outer contour 53. As shown in FIG. 1, the outer
contour 53 of mating part 50 is adapted to the inner contour
33 of holder so that the mating part may be secured or fixed
to the holder, especially in a position in which at least one
projection 55 of the mating part contacts and compresses the
elastomeric shaped part in the finally assembled status of the
present clamping device as described below.

As mentioned above, mating part 50 comprises at least
one projection 55 which is located or attached to the
downstream surface 51 of the mating part 50 so that the at
least one projection 55 projects into the (the inner lumen) of
holder 30 and contacts and deforms the elastomeric shaped
part 40 in its final and fully assembled position. In the
embodiment shown in FIG. 1, the at least one projection 55
already contacts the elastomeric shaped part 40, however, as
mating part 50 is not in its final and fully assembled position
and secured to the upstream end of holder 30, the at least one
projection 55 does not yet deform elastomeric shaped part
40. As mentioned above in connection with mating part 50,
projections 55 as shown in FIG. 1 may be part of the same
projection, e.g. a circular, ring-like structure, or maybe two
separate projections, e.g. two projections in the form of a
knob or a bar and located on opposite (lateral) ends of
mating part 50.

Elastomeric shaped part 40 of the device 10 of the present
invention further comprises at least one compensating sur-
face 45. As shown in FIG. 1 the at least one compensating
surface 45 does not contact the mating part 50 and/or the at least one projection 55 of mating part 50. In this context also, it should be noticed, however, that FIG. 1 does not depict device 10 in the assembled state in which mating part 50 is secured to holder 30 and fluidic component 20 is securely clamped by device 10. In the device shown in FIG. 1, fluidic component 20 and elastomeric shaped part 40 have already been introduced to the inner lumen of holder 30, however, mating part 50 and projection 55 is not in its final position yet.

As can be seen in the embodiment shown in FIG. 1, the compensating surface (or surfaces) 45 of elastomeric shaped part 40 is located at the downstream end 41 of elastomeric shaped part 40. Specifically, compensating surface (or surfaces) 45 of elastomeric shaped part 40 is not located at the upstream end 42 of elastomeric shaped part 40. Furthermore, in the embodiment shown in FIG. 1 compensating surface 45 is formed by that at least a part of the downstream surface 41 of elastomeric shaped part 40 is inclined or sloped (with regard to a plane perpendicular to the main axis X (see FIG. 2) of the device) towards the inner contour 43 of the elastomeric shaped part 40. In this arrangement, compensating surface 45 of elastomeric shaped part 40, together with the outer contour 23 of fluidic component 20 and the inner surface of downstream end 31 of holder 30 defines and confines a compensating volume 56 into which elastomeric shaped part 40 can expand when compressed by mating part 50 and/or the at least one protrusion 55 of mating part 50.

FIG. 2 shows the device 10 as shown in FIG. 1 in the assembled state in which mating part 50 is secured or fixed to holder 30, whereas some of the elements and components as described in FIG. 1 are omitted for clarity. Accordingly, FIG. 2 (as FIGS. 4 and 6) also depict embodiments of fluidic assembly 15 of the present invention. As can be seen, the at least one projection 55 as well as mating part 50 itself contact the upstream end of elastomeric shaped part 40. Thereby, the at least one projection 55 reaches into and thereby deforms elastomeric shaped part 40. Due to the distribution of the pressure exerted by protrusion 55 deforming elastomeric shaped part 40 at its upstream end or surface 42, elastomeric shaped part is deformed at the opposite side by dilation and expansion of the compensating surface 45 of the elastomeric shaped part 40 into the compensating volume 56 resulting in a reduction of the compensating volume (Vc). This, however, results in an even distribution of the pressure over the entire elastomeric shaped part 40, specifically of the entire inner contour 43 of the elastomeric shaped part 40 contacting the outer contour 23 of the fluidic component 20, thereby effectively and liquid- and pressure-tightly clamping the fluidic component 20 without the risk of damage to the clamped fluidic component 20.

Figure 3:
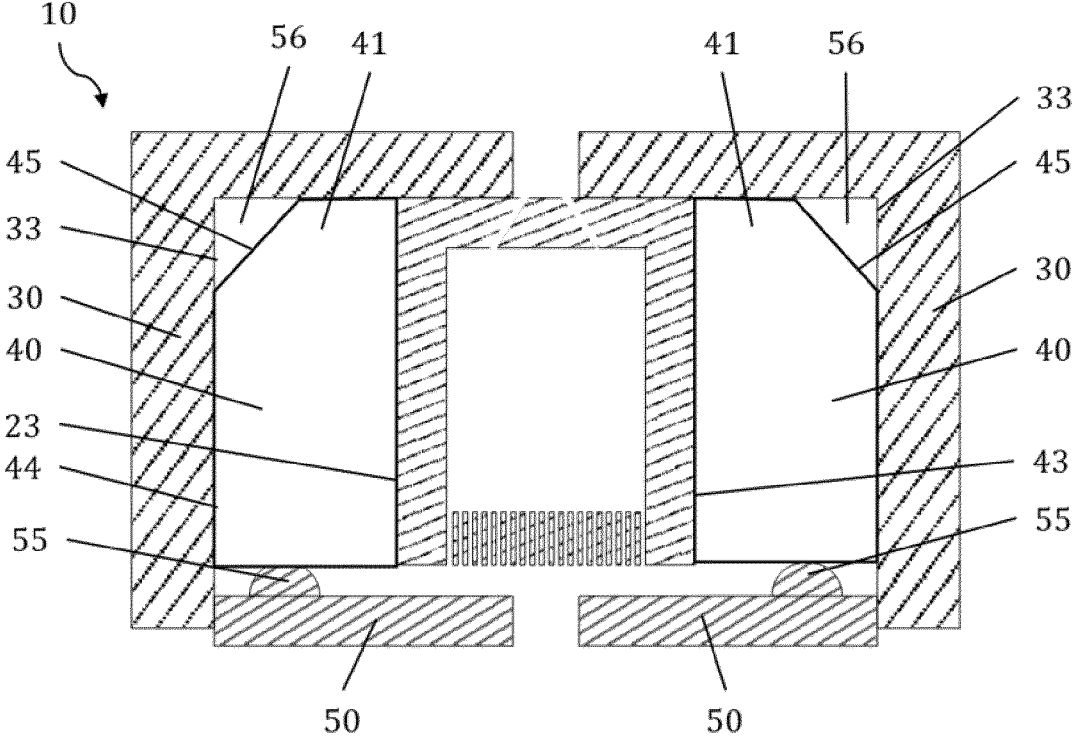
FIG. 3 depicts a device for clamping a fluidic component with an elastomeric shaped part having a compensating surface facing the inner contour of the holder prior to assembly.

FIG. 3 depicts another embodiment of a device 10 for clamping a fluidic component 20 with an elastomeric shaped part 40 having a compensating surface 45 facing the inner contour 33 of the holder 30 prior to assembly. As in FIG. 2, the components of the device correspond to those as described in FIG. 1, with some reference signs omitted to avoid redundancies. As mentioned above, according to the present embodiment the compensating surface 45, in this embodiment also, does not contact the mating part 50 and/or at least one projection 55 thereof in the partially assembled state and is located at the downstream end 41 of the elastomeric shaped part 40. In contrast to the embodiment shown in FIGS. 1 and 2, however, the compensating surface 45 of elastomeric shaped part 40 is formed by that at least a part of the downstream surface 41 of elastomeric shaped part 40 is inclined or sloped (with regard to a plane perpendicular to the main axis X of the device) towards the outer contour 44 of the elastomeric shaped part 40. In this arrangement, compensating surface 45 of elastomeric shaped part 40, together with the inner surface 33 of downstream end 31 of holder 30 defines and confines a compensating volume 56 into which elastomeric shaped part 40 can expand when compressed by mating part 50 and/or the at least one protrusion 55 of mating part 50. In this embodiment, the contact between the inner contour 43 of the elastomeric shaped part 40 is maximized from the beginning, as the inner contour 43 of the elastomeric shaped part completely contacts and encloses the outer contour 23 of the fluidic component 20.

Figure 4:
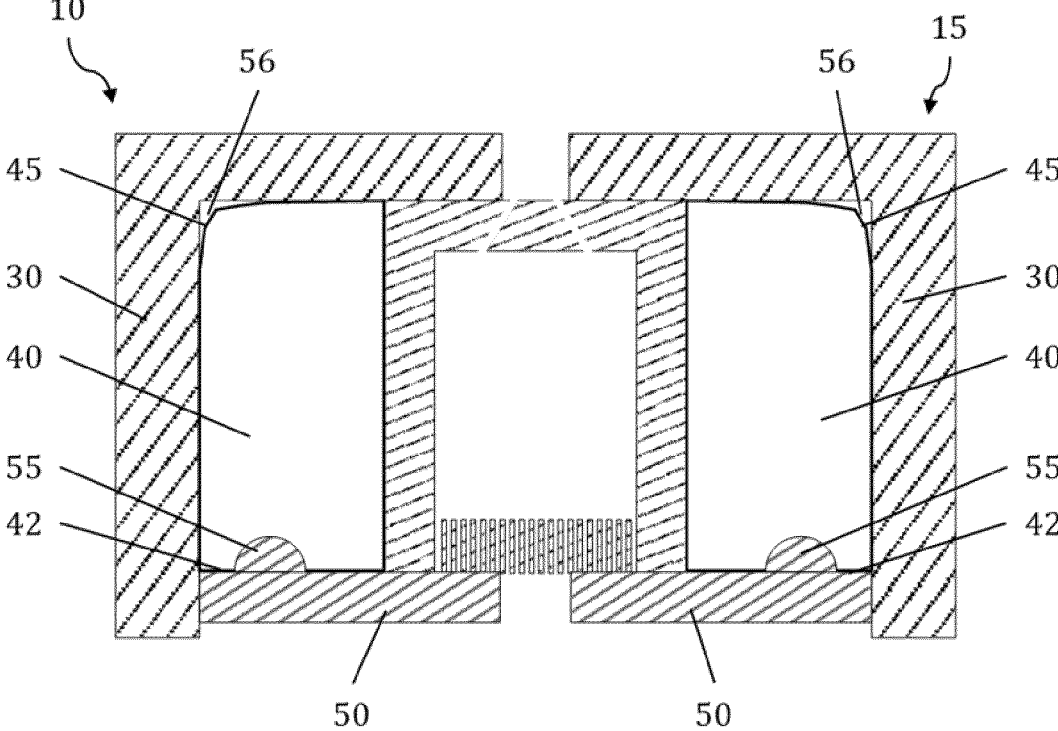
FIG. 4 shows the device of FIG. 3 as well as a fluidic assembly according to the present invention in the assembled state.

FIG. 4 depicts the device 10 of FIG. 3 in the assembled state in which mating part 50 is secured or fixed to holder 30, and accordingly an embodiment of fluidic assembly 15, whereas some of the elements and components as described in FIG. 1 are omitted for clarity. Just as in the embodiment as shown in FIG. 2, the at least one projection 55 as well as mating part 50 itself contact the upstream end of elastomeric shaped part 40. Thereby, the at least one projection 55 reaches into and thereby deforms elastomeric shaped part 40, or, more specifically the compensation surface 45 of elastomeric shaped part 40. Due to the distribution of the pressure exerted by projection 55 deforming elastomeric shaped part 40 at its upstream end or surface 42, elastomeric shaped part is deformed at the opposite side by dilation and expansion of the compensating surface 45 of the elastomeric shaped part 40 into the compensating volume 56 resulting in a reduction of the compensating volume (Vc).

Figure 5:
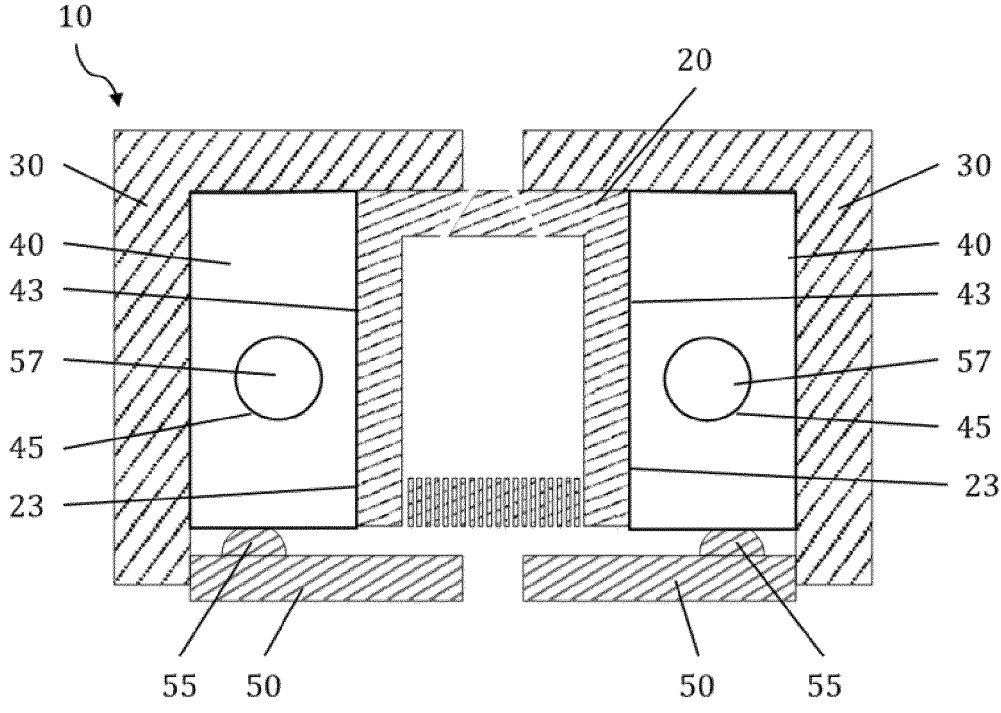
FIG. 5 depicts a device for clamping a fluidic component with an elastomeric shaped part having an interior compensating surface in the form of a hollow space located in the interior of the elastomeric shaped part prior to assembly.

FIG. 5 depicts a further embodiment of a device 10 for clamping a fluidic component with an elastomeric shaped part 40 having an interior compensating surface 45 in the form of a hollow space or inner compensating volume 57 located in the interior of the elastomeric shaped part 40 prior to final assembly. As in the embodiments shown in FIG. 3, the components of the device 10 correspond to those as described in FIG. 1, with some reference signs omitted to avoid redundancies.

As mentioned above, according to the present embodiment the compensating surface 45, in this embodiment also, does not contact the mating part 50 and/or at least one projection 55 thereof in the partially assembled state and is located in the interior of the elastomeric shaped part. In contrast to the embodiment shown in FIGS. 1 to 4, however, the compensating surface 45 of elastomeric shaped part 40 is formed by at least one hollow space located in the interior of the elastomeric shaped part and, accordingly, does not have contact to the surrounding atmosphere.

In this embodiment also, the contact between the inner contour 43 of the elastomeric shaped part 40 is maximized from the beginning, as the inner contour 43 of the elastomeric shaped part completely contacts and encloses the outer contour 23 of the fluidic component 20. Furthermore, the contact between all outer surfaces of the elastomeric shaped part 40 to the surrounding surfaces of the holder 30, the mating part 50 and the at least one protrusion 55 thereof as well as the liquid component 20 is maximized leading to an effective clamping and fixation of the fluidic component 20 in the assembled state. In this embodiment, the internal compensating surface 45 surrounding an internal compensating volume 57 is formed by a hollow annular space located in the interior of the elastomeric shaped part.

Figure 6:
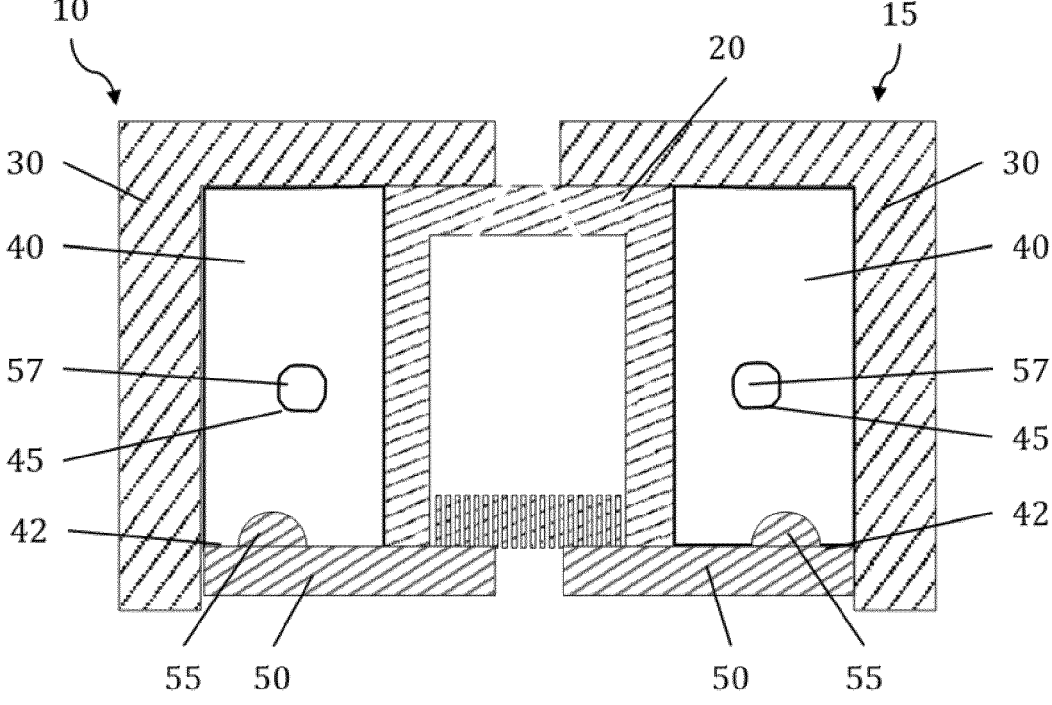
FIG. 6 shows the device of FIG. 5 as well as a fluidic assembly according to the present invention in the assembled state.

FIG. 6 depicts the device 10 of FIG. 5 in the assembled state in which mating part 50 is secured or fixed to holder 30 and, accordingly, a further embodiment of fluidic assembly 15, whereas some of the elements and components as described in FIG. 1 are omitted for clarity. Just as in the embodiment as shown in FIGS. 2 and 4, the at least one projection 55 as well as mating pert 50 itself contact the upstream end 42 of elastomeric shaped part 40. Thereby, the at least one projection 55 reaches into and thereby deforms elastomeric shaped part 40. Due to the distribution of the pressure exerted by projection 55 deforming elastomeric shaped part 40 at its upstream end or surface 42, elastomeric shaped part is deformed internally by expansion of the internal compensating surface 45 of the elastomeric shaped part 40 into the internal compensating volume 57 resulting in a reduction of the internal compensating volume (Vc).

In all embodiments shown in FIGS. 1 to 6 the compensating volume 56 or internal compensating volume 57 is (slightly) larger than the overall volume Vp of the at least one projection 55 resulting in a remaining smaller compensating volume 56 or internal compensating volume 57 after complete and final assembly of the device by securing the mating part 50 to the holder 30.

Figure 7:
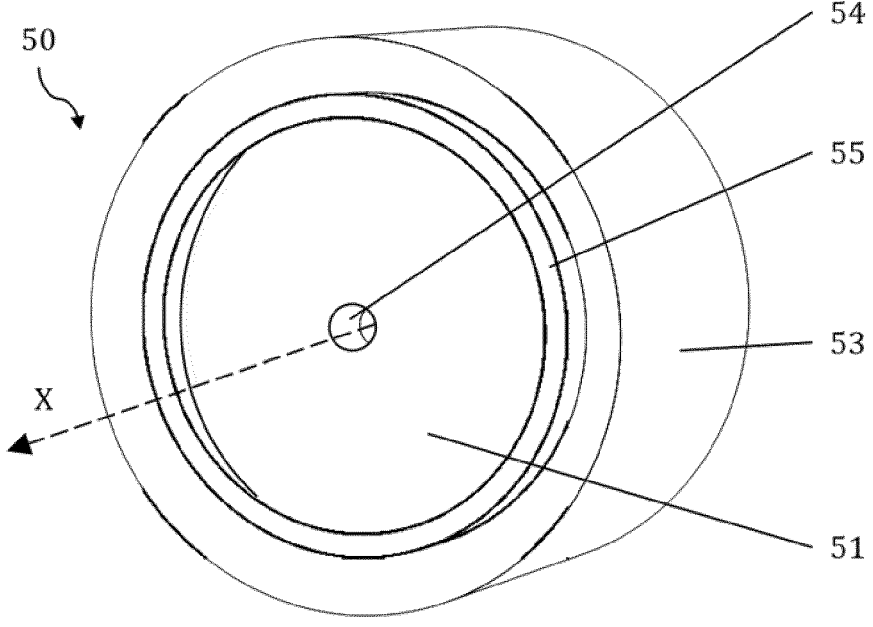
FIG. 7 shows a perspective view of one embodiment of the mating part having a continuous circular projection.

FIG. 7 shows a perspective view of one embodiment of the mating part 50 having a continuous circular projection 55. Mating part 50 as shown in FIG. 7 has downstream surface 51, an outer contour or surface 53 as well as a fluid opening 54 which allows for the passage of a fluid or liquid to be conveyed to the fluidic component to be clamped by the clamping device of the present invention. On the downstream surface 51 of the mating part 50 a circular projection 55 is provided in the form of an annular ring centered around the main rotational axis X of the present clamping device.

Figure 8:
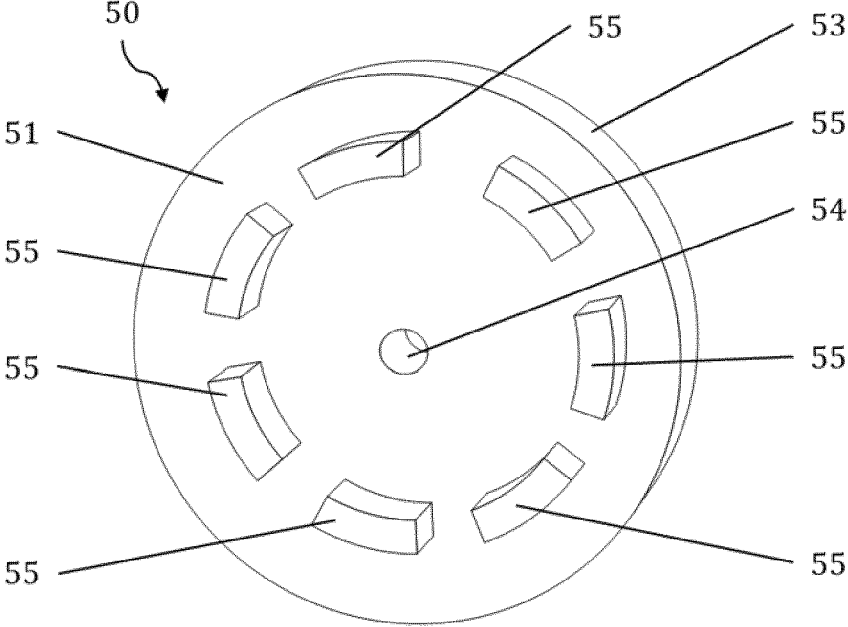
FIG. 8 shows a perspective view of one embodiment of the mating part having a plurality of projections arranged in the form of a discontinuous circular ring.

FIG. 8 shows a perspective view of one alternative embodiment of the mating part 50. In this embodiment, the continuous circular projection 55 as shown in the embodiment of FIG. 7 has been replaced by a plurality of projections 55 arranged in the form of a discontinuous circular ring, as in FIG. 7, centred around the main rotational axis X (see FIG. 7). As can be seen in FIG. 8, all of the plurality of projections 55 have an equal hight and width.

Figure 9:
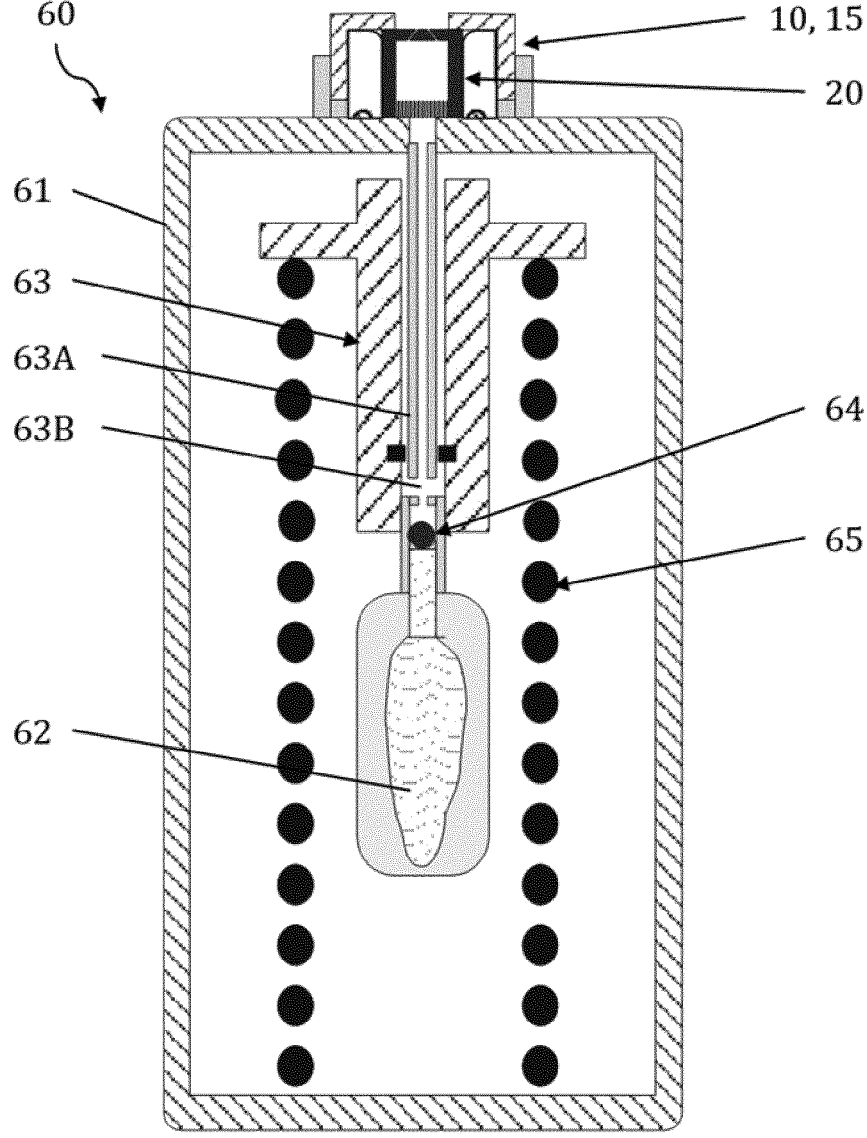
FIG. 9 shows a schematic cut view of an exemplary inhalation device for the inhalative administration of a medically active liquid in nebulized form comprising a clamping device for clamping a fluidic component.

In FIG. 9, a schematic cut view of an exemplary inhalation device 60 for the inhalative administration of a medically active liquid in nebulized form is shown, comprising a clamping device 10, or, more specifically, a fluidic assembly 15 comprising such clamping device. The inhalation device 60 comprises a housing 61, which is preferably shaped and dimensioned such that it can be held with one hand and can be operated by one finger, e.g. the thumb (not shown). A reservoir 62 for storage of a medically active liquid is located inside the housing 61. The depicted reservoir 62 is designed to be collapsible; that means that during proceeding emptying, the elastic or at least limp walls buckle, so that the under-pressure which is necessary for extraction of a certain amount of liquid is not, or almost not, increased. Further, the inhalation device 60 comprises a pumping unit 63 within the housing 61 with a piston 63A and a pumping chamber 63B for generation of the desired pressure which is necessary for emitting the medically active liquid and nebulizing the same. The pumping chamber 63B is fluidically connected with reservoir 62 by means of an inlet check valve 64. Check valve 64 serves for allowing inflow of the medically active liquid into the pumping chamber 63B and blocks a back flow of the liquid into reservoir 62 upon release of a not-depicted locking mechanism. As a means for the storage and delivery of potential energy, a spring 65 is provided which is coupled with one (upwards directed) end to the pumping unit 63 and which is supported at housing 61 (lower part of the figure).

The clamping device 10 or fluidic assembly 15, comprising a fluidic component or, more specifically, nozzle 20, is placed on the upper edge of the housing 61 of the inhalation device 60 such that the nozzle 20 is in fluid connection with the pumping unit. In the shown embodiment, the mating part is formed by the outer surface of housing 61. In further embodiments, however, it is also possible to design mating part 50 as a separate element as shown in previous FIGS. 1 to 8 and to attach such mating part 50 or fluidic assembly 15 to inhalation device 60.

LIST OF REFERENCE NUMERALS

10 clamping device
15 fluidic assembly
20 fluidic component, nozzle
21 downstream end of the fluidic component
22 upstream end of the fluidic component
23 outer contour of the fluidic component
24 ejection channels of the fluidic component
30 holder
31 downstream end of the holder
32 upstream end of the holder
33 inner contour of the holder
34 outlet opening of the holder
35 sidewall of the holder
36 access opening of the holder
40 elastomeric shaped part
41 downstream end of elastomeric shaped part
42 upstream end of elastomeric shaped part
43 inner contour of the elastomeric shaped part
44 outer contour of the elastomeric shaped part
45 compensating surface of the elastomeric shaped part
50 mating part
51 downstream surface of the mating part
52 upstream surface of the mating part
53 outer contour of the mating part
54 fluid opening of the mating part
55 projection of the mating part
56 compensating volume
57 internal compensating volume
X main rotational axis of device
60 inhalation device
61 housing
62 reservoir filled with medical liquid
63 pumping unit
63A piston
63B pumping chamber
64 valve
65 spring

What is claimed is:

1. A device for clamping a fluidic component which is subjected to a fluctuating fluid pressure, said fluidic component having a downstream end, an opposite upstream end and an outer contour, said device comprising a holder having a downstream end and an opposite upstream end and an inner contour, wherein in a partially assembled state the fluidic component is arranged inside the holder and wherein the downstream end of the fluidic component is supported by the downstream end of the holder, an elastomeric shaped part having a downstream end and an opposite upstream end and an inner contour and an outer contour, wherein the inner contour of the elastomeric shaped part is configured to enclose and contact the outer contour of the fluidic component, and a mating part adapted to be secured to the upstream end of the holder, wherein the mating part has an downstream end and an opposite upstream end and an outer contour, wherein the outer contour of the mating part is adapted to the inner contour of the holder, and wherein the mating part comprises at least one projection, and wherein the at least one projection projects into the holder and contacts and deforms the elastomeric shaped part, wherein the elastomeric shaped part comprises at least one compensating surface that, prior to the assembled state, defines a hollow space between the at least one compensating surface and at least the holder at the downstream end of the elastomeric shaped part or the at least one compensating surface comprises an internal compensating volume within the elastomeric shaped part into which the elastomeric shaped part expands in the assembled state, and wherein the at least one compensating surface in the assembled state does not contact the mating part or the at least one projection of the mating part.

2. The device according to claim 1, wherein the at least one compensating surface is located in an interior of the elastomeric shaped part.

3. The device according to claim 1, wherein the at least one compensating surface is a surface or surface area of the elastomeric shaped part that is configured to deform due to contact with the mating part or the at least one projection of the mating part in the assembled state.

4. The device according to claim 1, wherein the at least one compensating surface is not located at the upstream end of the elastomeric shaped part.

5. The device according to claim 1, wherein the at least one compensating surface is formed by at least a part of a surface of the downstream end of the elastomeric shaped part and is inclined or sloped towards the inner and/or the outer contour of the elastomeric shaped part.

6. The device according to claim 1, wherein the at least one compensating surface is formed by at least a part of a surface of the downstream end of the elastomeric shaped part and is inclined or sloped with regard to a plane perpendicular to a main axis of the device towards the inner contour of the elastomeric shaped part.

7. The device according to claim 1, wherein the internal compensating volume is formed by a hollow annular space located in an interior of the elastomeric shaped part.

8. The device according to claim 1, wherein the internal compensating volume is formed by a plurality of hollow annular spaces located in an interior of the elastomeric shaped part.

9. The device according to claim 1, wherein the at least one projection of the mating part has the form of at least one annular ring.

10. The device according to claim 1, wherein the at least one projection of the mating part is in the form of a plurality of projections.

11. The device according to claim 10, wherein the plurality of projections has an equal height and/or width.

12. The device according to claim 1, wherein the at least one projection has an overall volume Vp and wherein the hollow space defines a compensating volume or the internal compensating volume that has an overall volume Vc, and wherein the overall volume Vp of the at least one projection is based on to the overall volume Vc of the compensating volume or the internal compensating volume.

13. The device according to claim 12, wherein the overall volume Vp of the at least one projection amounts to from about 10% to about 50% of the overall compensating volume Vc.

14. The device according to claim 1, wherein a entire surface of the upstream end of the elastomeric shaped part in its entirety contacts a downstream surface of the mating part and/or of the at least one projection.

15. The device according to claim 1, wherein the fluidic component is a nozzle for nebulization or aerosolization of a liquid.

16. The device according to claim 1, wherein the fluidic component is a nozzle for nebulization or aerosolization of a medically active liquid to be administered to a subject in need thereof by inhalation.

17. The device according to claim 1, wherein the fluidic component is an impingement nozzle.

18. The device according to claim 1, wherein the fluidic component has a cylindrical or rectangular shape.

19. The device according to claim 1, wherein the device is adapted for clamping a plurality of the fluidic components.

20. The device according to claim 1, wherein the elastomeric shaped part comprises or consists essentially of synthetic rubbers, fluoropolymeric materials, nitrile butadiene rubber (NBR), ethylene propylene diene monomer rubber (EPDM), polytetrafluorethylene (PTFE), silicone, or liquid silicone rubber (LSR).

21. The device according to claim 1, wherein the holder and/or the mating part and/or the at least one protrusion comprises or consists essentially of stainless steel, polyethylene, polystyrene, polyether ether ketone (PEEK), acrylonitrile butadiene styrene (ABS), polycarbonate, or polyamide.

22. A fluidic assembly comprising the device for clamping the fluidic component according to claim 1 and the fluidic component clamped by the device.

23. The fluidic assembly of claim 22, wherein the device for clamping the fluidic component is a nozzle holder and the fluidic component is a nozzle.

24. An inhalation device for the inhalative administration of a medically active liquid in nebulized form, wherein the inhalation device comprises the device according to claim 1.

25. A method for clamping the fluidic component or for the manufacture of a fluidic assembly comprising the device for clamping the fluidic component according to claim 1 and the fluidic component clamped by the device, the method comprising the steps of:
  a) providing components of the device for clamping the fluidic component according to claim 1, comprising
    the holder;
    the elastomeric shaped part having the at least one compensating surface;
    the fluidic component; and
    the mating part comprising the at least one projection;
  b) assembling the device by:
    b1) introducing the elastomeric shaped part into the holder and, subsequently, introducing the fluidic component into the elastomeric shaped part, or
    b2) introducing the fluidic component into the elastomeric shaped part and, subsequently, introducing the elastomeric shaped part holding the fluidic component into the holder; and
  c) securing the mating part to the holder and thereby compressing the elastomeric shaped part by contacting the at least one protrusion of the mating part with an upstream surface of the elastomeric shaped part.

* * * * *